US011617905B2

(12) United States Patent
Fulbrook

(10) Patent No.: US 11,617,905 B2
(45) Date of Patent: Apr. 4, 2023

(54) ULTRAVIOLET LIGHT DISINFECTING FACE SHIELD SYSTEM

(71) Applicant: Efficiency Products, LLC, Fairfax, VA (US)

(72) Inventor: Jim E. Fulbrook, Fairfax, VA (US)

(*) Notice: Subject to any disclaimer, the term of this patent is extended or adjusted under 35 U.S.C. 154(b) by 0 days.

(21) Appl. No.: 17/695,689

(22) Filed: Mar. 15, 2022

(65) Prior Publication Data

US 2022/0202982 A1     Jun. 30, 2022

Related U.S. Application Data

(63) Continuation-in-part of application No. PCT/US2021/029652, filed on Apr. 28, 2021.

(Continued)

(51) Int. Cl.
*A62B 18/00* (2006.01)
*A61L 9/20* (2006.01)
*A61L 9/22* (2006.01)
*A62B 18/02* (2006.01)
*A62B 18/08* (2006.01)

(52) U.S. Cl.
CPC .............. *A62B 18/006* (2013.01); *A61L 9/20* (2013.01); *A61L 9/205* (2013.01); *A61L 9/22* (2013.01); *A62B 18/003* (2013.01); *A62B 18/02* (2013.01); *A62B 18/08* (2013.01); *A61L 2209/111* (2013.01); *A61L 2209/12* (2013.01); *A61L 2209/133* (2013.01); *A61L 2209/134* (2013.01);
(Continued)

(58) Field of Classification Search
CPC .... A62B 7/00; A62B 7/10; A62B 9/00; A62B 9/04; A62B 18/00; A62B 18/003; A62B 18/006; A62B 18/02; A62B 18/04; A62B 18/045; A62B 18/08; A62B 18/082; A62B 18/084; A62B 18/10; A62B 19/00; A62B 23/00; A61L 9/20; A61L 9/205; A61L 9/22; A61L 2209/133; A61L 2209/134; A61L 2209/212; A41D 13/11; A42B 3/22; A42B 3/221; A61F 9/06
See application file for complete search history.

(56) References Cited

U.S. PATENT DOCUMENTS 4,462,399 A    7/1984   Braun
6,233,748 B1   5/2001   Gieger et al.
(Continued)

FOREIGN PATENT DOCUMENTS

WO      2019175694 A1    9/2019
WO      WO-2022109630 A1 *   5/2022

*Primary Examiner* — Colin W Stuart

(57) ABSTRACT

A face shield system utilizes a headgear with an outer shield and an optional inner side that is proximal to a person wearing the face shield. The headgear may be configured to receive a disinfecting cartridge that neutralize or destroy pathogens in an airflow flowing therethrough. The cartridge may include a neutralizing UV light emitter and a destroying UV light emitter as well as an ionizer. The plenum may include a plurality of baffles to produce a serpentine flow through the plenum. The baffles and the interior of the plenum may be textured and polished and may include catalytic coatings for improving the effectiveness of pathogen destruction and absorbing ions and UV light. An air inlet may allow air from the plenum to pass into the inner side of the shield after the air is disinfected and purified by the UV light emitters.

25 Claims, 12 Drawing Sheets

Related U.S. Application Data

Figure 1:
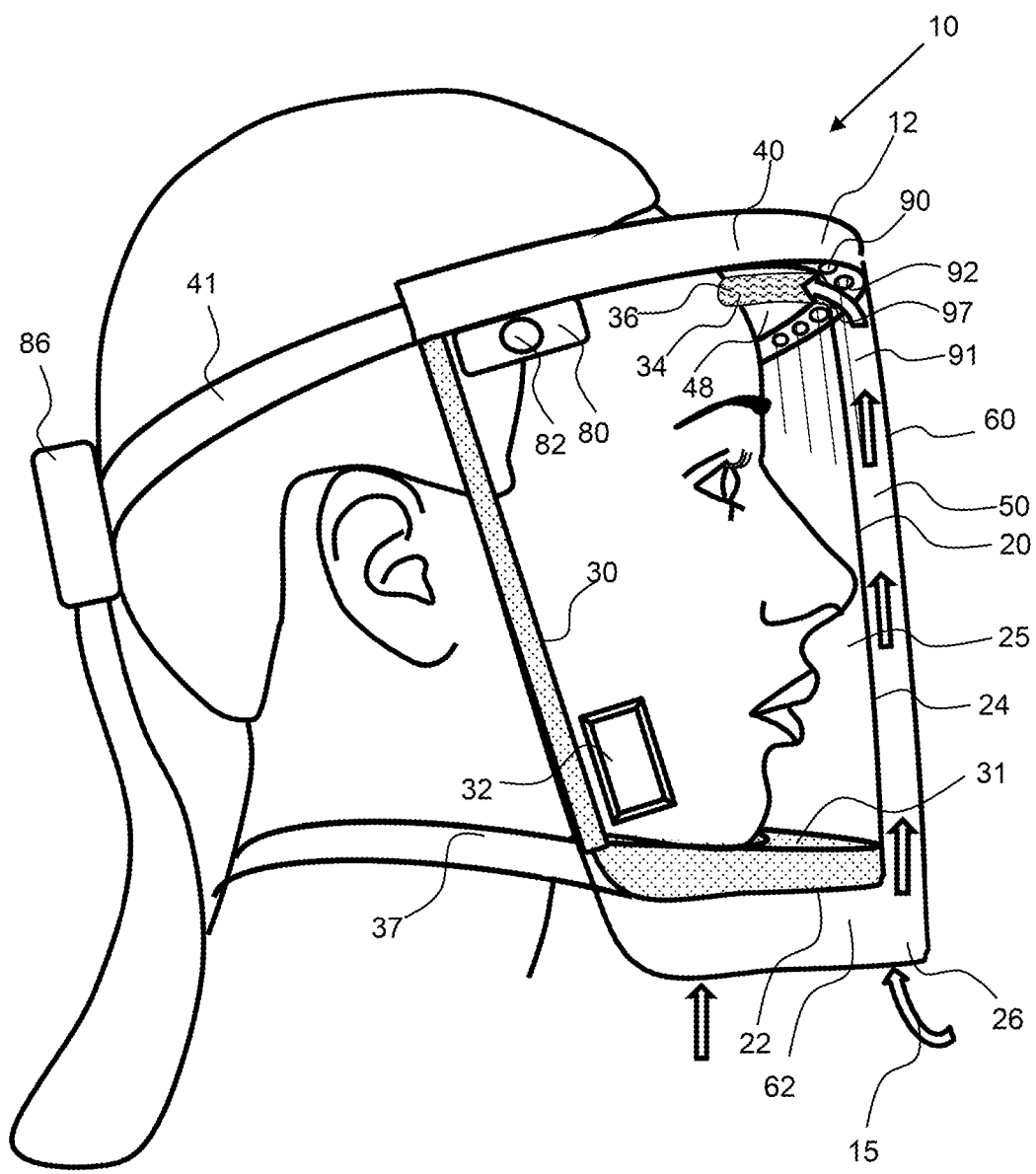

(60) Provisional application No. 63/016,966, filed on Apr. 28, 2020, provisional application No. 63/026,003, filed on May 16, 2020.

(52) U.S. Cl.
CPC ....... *A61L 2209/14* (2013.01); *A61L 2209/15* (2013.01); *A61L 2209/212* (2013.01)

(56) References Cited

U.S. PATENT DOCUMENTS

| | | |
|---|---|---|
| 8,574,331 B2 | 11/2013 | Bangera et al. |
| 8,733,356 B1 | 5/2014 | Roth |
| 11,458,338 B2 * | 10/2022 | Wilson ................. A62B 18/003 |
| 11,524,084 B2 * | 12/2022 | Tung ................. A41D 13/1192 |
| 2007/0050898 A1 | 3/2007 | Larson et al. |
| 2009/0004047 A1 | 1/2009 | Hunter et al. |
| 2017/0173371 A1 | 6/2017 | Truex et al. |
| 2018/0084848 A1 | 3/2018 | Pavalarajan et al. |
| 2020/0001123 A1 | 1/2020 | VanDerWoude et al. |
| 2020/0030469 A1 | 1/2020 | Neister et al. |
| 2021/0339061 A1 * | 11/2021 | Fajardo ................. A62B 18/08 |
| 2021/0353969 A1 * | 11/2021 | Leschinsky ............. A62B 9/00 |
| 2021/0378323 A1 * | 12/2021 | Zamuruyev .......... A62B 18/006 |
| 2022/0118290 A1 * | 4/2022 | Delgatty ................ A62B 18/02 |
| 2022/0218062 A1 * | 7/2022 | Perry ................... A42B 1/017 |
| 2022/0257822 A1 * | 8/2022 | Nasui ....................... B03C 3/32 |

\* cited by examiner

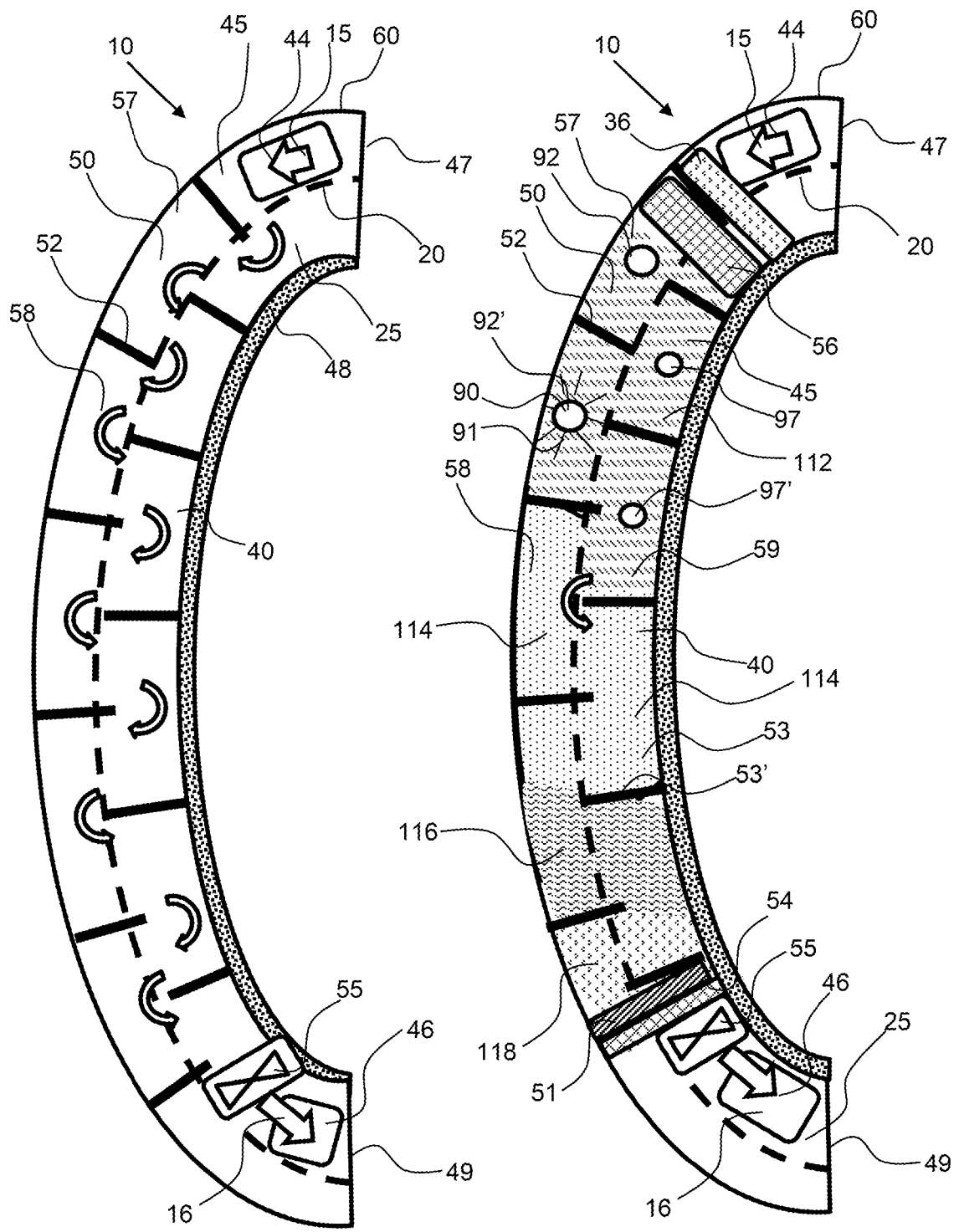

ULTRAVIOLET LIGHT DISINFECTING FACE SHIELD SYSTEM

CROSS REFERENCE TO RELATED APPLICATIONS

This application is a continuation in part of PCT application No. PCT/US21/29652, filed on Apr. 28, 2021 and currently pending, which claims the benefit of priority to U.S. provisional patent application No. 63/016,966 filed on Apr. 28, 2020, and also to U.S. provisional patent No. 63/026,003 filed on May 16, 2020; all of these former applications are hereby incorporated by reference herein.

BACKGROUND OF THE INVENTION

Field of the Invention

The invention relates to an ultraviolet (UV) light disinfecting face shield system that is configured to disinfect breathing air and block pathogens.

Background

Personal Protective Equipment (PPE) for shielding a person from pathogens include face shields and face masks. The face shield is worn to protect the wearer from contact with droplets and bodily fluid that might contain a virus and the mask is worn to filter the breathing air. The mask covers the person's mouth and nose, thereby making it difficult to speak and breath and making it more difficult for others to hear the wearer speaking. Most current face shields are "passive" in that they only provide a barrier or filter.

SUMMARY OF THE INVENTION

The invention is directed to a face shield system comprising a headgear with an outer shield and UV light emitters that emit light on an inner side, side proximal to a person wearing the face shield, to neutralize or destroy pathogens. An "active" PPE system is one that provides a disinfection system such as UV light that has been shown to be effective in destroying pathogens such as viruses, bacteria, and fungi. Since the outbreak of the COVID-19 pandemic, there is an urgent need for active PPE systems that effectively and safely disinfect the air users breathe on a continuous basis.

An exemplary face shield system may also include an inner shield configured more proximal to the wearer's face than the outer shield, thereby forming a plenum between the outer and inner shields where the UV light is emitted. The inner shield may comprise a UV light protection barrier, such as a coating or film layer that filters out or blocks UV light from passing through. A destroying UV light emitter may emit a destroying UV light down the plenum when the inner face shield is attached to the headgear. An air inlet may allow air from the plenum to pass into the inner side, a side proximal to a person wearing the face shield, of the inner shield. In this way, air may enter the plenum, travel up along the plenum toward the UV light emitters and be neutralized or destroyed by the UV light prior to passing through the air inlet into the inside of the inner shield where the air can be safely inhaled. A face gasket may extend around a portion of a person's face and may include a chin gasket portion. The headgear may have a head gasket for sealing along the person's head when donned. The headgear along with face gasket and chin gasket may effectively seal a person's face within the inner shield, thereby effectively preventing air from entering into the inner shield area except from the air inlet, wherein at least 90% of the inhaled air is from the air inlet and preferably at least 95% or more or even 99% or more, under relaxed breathing conditions.

Note that when a specific wavelength is mentioned such as 222 nm (nanometers), it is the dominant wavelength in a relatively narrow band emitted by the UVC source where other wavelengths are also emitted but in lesser photon numbers. Each narrow band emitter has its own dominant wavelength and emission bands that are specific to the emitter. The 222 nm narrow band UVC emitter is important as one of the sources because this narrow UVC band has been shown to be relatively safe for use around humans since it does not penetrate the skin below the dead skin (epidermis) layer and does not penetrate the outer layers of the eyeball as well.

An exemplary face shield system may comprise a plurality of UV light emitters, wherein some of the emitters emit a skin safe or neutralizing UV light, such as UV light having a wavelength of about 222 nm and some emit a destroying UV light having a wavelength of about 270 nm. An exemplary UV light may have wavelength within the ultraviolet germicidal irradiation (UVGI) range or from about 200 nm to about 300 nm. A wavelength that is substantially a specific value, such as 222 nm, may have a range around the specific value of about 10 nm or less, about 5 nm or less, and preferably by 2 nm or less and most preferably by 1 nm or less. A neutralizing UV light may prevent any pathogens, such as a virus from replicating and thereby prevent infection by the virus while a destroying UV light may destroy the virus by breaking one or more molecular bonds in the RNA or DNA of the virus. An exemplary face shield system may comprise a controller that enables a user to select which type of UV light they want emitted. In a high-risk location, such as when directly caring for an infected person or patient, a user may switch over to a destroying UV light and when in lower risk location, such as in other areas of a hospital or care facility, they may switch over to a neutralizing UV light. An exemplary face shield system may comprise an inner shield receiver in the headgear to allow detachable attachment of the inner shield to the headgear. The inner shield may also have other structures such as tubes or barriers that further protect the user from exposure to harmful UVC light. An inner shield detector may be coupled with a controller and the controller may only enable the destroying UV light to be emitted when the inner shield is attached, as this provides protection of the person's face from the destroying UV light. A user may use a user interface, such as a button to switch from destroying to neutralizing UV light.

An inner face shield may comprise a face gasket that extends down along the sides of the inner face shield to form an effective seal along the person's face and may comprise a chin gasket that seals along the person's chin or along the front part of the person's neck. The face gasket may produce a barrier from air entering the inside area of the inner shield, or on the inner side of the inner shield, and breathing air may be drawn through the air plenum between the inner and outer shields through the air inlet and into the inside area of the inner shield; the area between the inner shield and a person's face. A face gasket may allow a person to move their chin and retain an effective seal. A face gasket may include foam or an elastomeric material that conforms to the person's face contours.

An air inlet may be configured in the inner face shield, such as proximal to the top of the inner face shield, wherein the breathing air has to travel up along the plenum and be exposed to the UV light before passing through the air inlet. The air inlet in the inner shield may comprise an inlet filter that filters out particles and droplets and may also shield UV light from passing therethrough. An inlet filter may be woven or non-woven material for example. The air inlet may be configured over a person's forehead when donned and therefore would not block a wearer's vision.

Alternatively, an air inlet may be configured in the headgear in the space between the inner and outer shields and lead to the headgear plenum, a space within the headgear that extends from the air inlet to the air outlet for passing air from the plenum to the inside of the inner shield. The headgear air inlet may be configured around the UV light emitters, thereby requiring the breathing air to pass very close to the UV light source where it will be most effective at neutralizing or destroying pathogens. A plurality of individual apertures or holes may be configured in the headgear as air inlets to disperse the openings over and around the UV emitters. The air inlet may extend into a headgear plenum which extends to headgear air outlet, or into the inside area of the inner shield where the breathing air can be inhaled.

A person may exhale air into the inside area of the inner shield and this exhaled air may escape through one-way exhaust valves in the inner shield, or face gasket. An exhaust valve may be a flap or flaps that open when the pressure in the inside area of the inner shield exceeds some threshold pressure. An exhaust valve may also include an exhaust filter to filter out any air that might enter from the outside into the inside area of the inner face shield. For both intake and exhaust air, an exemplary face shield system may have small fans to assist with air flow.

From: https://en.wikipedia.org/wiki/Ultraviolet

Ultraviolet (UV) is electromagnetic radiation with wavelength from 10 nm (with a corresponding frequency of approximately 30 PHz) to 400 nm (750 THz), shorter than that of visible light but longer than X-rays. Short-wave ultraviolet light damages DNA and sterilizes surfaces with which it comes into contact.

Short-wave ultraviolet light damages DNA and sterilizes surfaces with which it comes into contact. For humans, suntan and sunburn called erythema are familiar effects of exposure of the skin to UV light, along with an increased risk of skin cancer. The amount of UV light produced by the Sun means that the Earth would not be able to sustain life on dry land if most of that light were not filtered out by the atmosphere. More energetic, shorter-wavelength "extreme" UV below 121 nm ionizes air so strongly that it is absorbed before it reaches the ground. However, ultraviolet light (specifically, UVB) is also responsible for the formation of vitamin D in most land vertebrates, including humans. The UV spectrum thus has effects both beneficial and harmful to life.

The lower wavelength limit of human vision is conventionally taken as 400 nm, so ultraviolet rays are invisible to humans, although some people can perceive light at slightly shorter wavelengths than this. Insects, birds, and some mammals can see near-UV (i.e. slightly shorter wavelengths than humans can see)

The electromagnetic spectrum of ultraviolet radiation (UVR), defined most broadly as 10-400 nanometers (nm), can be subdivided into a number of ranges recommended by the ISO standard ISO-21348:

TABLE 1

UV Light Spectrum

| Name | Abbreviation | Wavelength (nm) | Photon energy (eV, aJ) | Notes/alternative names |
|---|---|---|---|---|
| Ultraviolet A | UVA | 400-315 | 3.10-3.94 (0.497-0.631) | Long-wave, black light, not absorbed by the ozone layer: soft UV |
| Ultraviolet B | UVB | 315-280 | 3.94-4.43 (0.631-0.710) | Medium-wave, mostly absorbed by the ozone layer: intermediate UV; Dorno [de] radiation |
| Ultraviolet C | UVC | 280-100 | 4.43-12.4 (0.710-1.987) | Short-wave, germicidal, completely absorbed by the ozone layer and atmosphere: hard UV |

The face shield system of the present invention may utilize UV emitters that emit UVA, UVB and/or UVC. In an exemplary system, the face shield utilizes UVC light that is at two or more different wavelengths, such as about 230 nm or less, 222 nm or less or 200 nm or less for neutralizing pathogens and may also emit UVC that is about 280 nm or less. In some cases, UVB light may be emitted, such as 315 nm or less. Any range of wavelengths may be emitted by one or more of the UV emitters of the face shield system.

An exemplary UV light that may be emitted as far-UVC light (207-222 nm) as it efficiently inactivates viruses and bacteria, neutralizes them, and is not harmful to exposed mammalian skin or eyes. Some far-UVC light wavelengths are unique by having strong absorbance in biological materials, but the unique UVC light does not penetrate deeper than the outer dead layers of human skin or into the eyes. It is absorbed by bacteria and viruses however as these organisms have micrometer or smaller dimensions, but they readily enable far-UVC to penetrate their outer layers and inactivate them by breaking or bending molecular bonds in DNA and RNA strands. Another exemplary range of UV light wavelength is defined as UVGI (UV Germicidal irradiation) which includes the 270 nm wavelength—defined as 254-270 nm, or for the purposes of this application from about 240 nm to 280 nm, or from about 245 nm to 275 nm. A key feature to this invention is the use of two narrow-band Light Emitting Diodes (LEDs) in the range of about 222 nm to neutralize pathogens and about 270 nm that would destroy the pathogens by being absorbed at and breaking molecular bonds in the DNA or RNA strands.

The inner shield may be detachably attachable to the headgear by insertion and removal into the inner shield receiver, such as into a ball and detent arrangement. An inner shield sensor may be configured to sense when the inner shield is inserted into the inner shield receiver and the sensor may be coupled with the controller to control what type of UV light is emitted.

An exemplary ultraviolet light disinfecting face shield system may comprise a breathing air disinfecting cartridge, which may be configured within a headgear plenum and have a headgear air inlet for receiving breathing air from the air plenum between the inner and outer shields. The breathing air disinfecting cartridge may be detachably attachable to the headgear plenum. The headgear plenum may have a serpentine airflow channel formed by an arrangement of headgear plenum baffles and a plurality of UV light emitters to disinfect the breathing air before exiting through the headgear air outlet and into the inside area of the inner shield for breathing. A serpentine airflow channel is an airflow channel that forces the airflow to change directions throughout the channel and flow in a non-linear path or back and forth, whereby the length of the airflow through the channel is increased over the shortest distance from the inlet to the outlet due to the directional changes, by at least 20%, and preferably 40% or more or even more preferably 60% or more. This increased resonance time in the airflow channel may more effectively enable the UV light to disinfect the breathing air. Research has shown that when pathogens are exposed to UVC/UVGI light for 100 milli-seconds or more, over 99.9% of the pathogens will be neutralized. The headgear plenum may extend along a front of an ultraviolet light disinfecting face shield system, or over a person's forehead when donned or may extend around a portion of the person's head. The headgear plenum may extend around the back of a person's head or along the head strap from a first side of the face shield to the opposing second side of the face shield, for example. The UV light emitters may emit light into the headgear plenum and the UV light may be substantially retained within the headgear plenum, wherein no direct UV light from a UV light emitter is emitted out of the headgear plenum.

An exemplary breathing air disinfecting cartridge, or headgear plenum may comprise a plurality of UV light emitters that emit UV light into the airflow channel from a headgear plenum inlet to a headgear plenum outlet. An ionizer may be configured proximal to the headgear plenum air inlet to introduce ions into the airflow. The ions may more effectively aid in disinfecting and purifying the air by also removing allergens as it flows through the airflow channel. An arrangement of baffles produces a serpentine airflow channel that increase the resonance time of the breathing air within the breathing air disinfecting cartridge or headgear plenum.

The interior of the headgear plenum may be coated with a UV catalyst that is configured to receive the emitted UV light. An exemplary ultraviolet disinfecting cartridge system may include a reactive material configured in the ultraviolet disinfecting cartridge, such as titanium dioxide that in the presence of UV light, is reactive with organic compounds, such as pathogens. Titanium dioxide is an example of a photocatalyst and other known photocatalyst may be used in the ultraviolet disinfecting cartridge to react with pathogens. A reactive material may be coated onto the interior of the ultraviolet disinfecting cartridge including the inside surface walls and the baffle surfaces.

The interior of the headgear plenum may be configured with a reflective material to reflect the UV light to increase the effectiveness of the light neutralizing or destroying pathogens. The UV light may be prevented from exiting the headgear plenum by a filter or baffles and the like.

An exemplary ultraviolet disinfecting cartridge may include an ionizer that is configured proximal to the inlet to produce disinfecting ionization of particulate matter and pathogens in the flow channel and may produce a minimal amount of ozone, which is also known to react with organic compounds, such as pathogens to disinfect the breathing air and/or exhalation air. A filter may be configured within the headgear plenum and may be proximal to the headgear plenum air outlet. The filter may be configured to remove particles and aerosol droplets from the breathing airflow before it enters into the inside area for breathing. The ionizer and/or filter may be replaceable from the breathing air disinfecting cartridge. The head gasket extends along the inside of the headgear plenum to form a seal along a person's head when donned. The ionizer and/or filter may effectively block UV light from exiting the headgear plenum.

Figure 3:
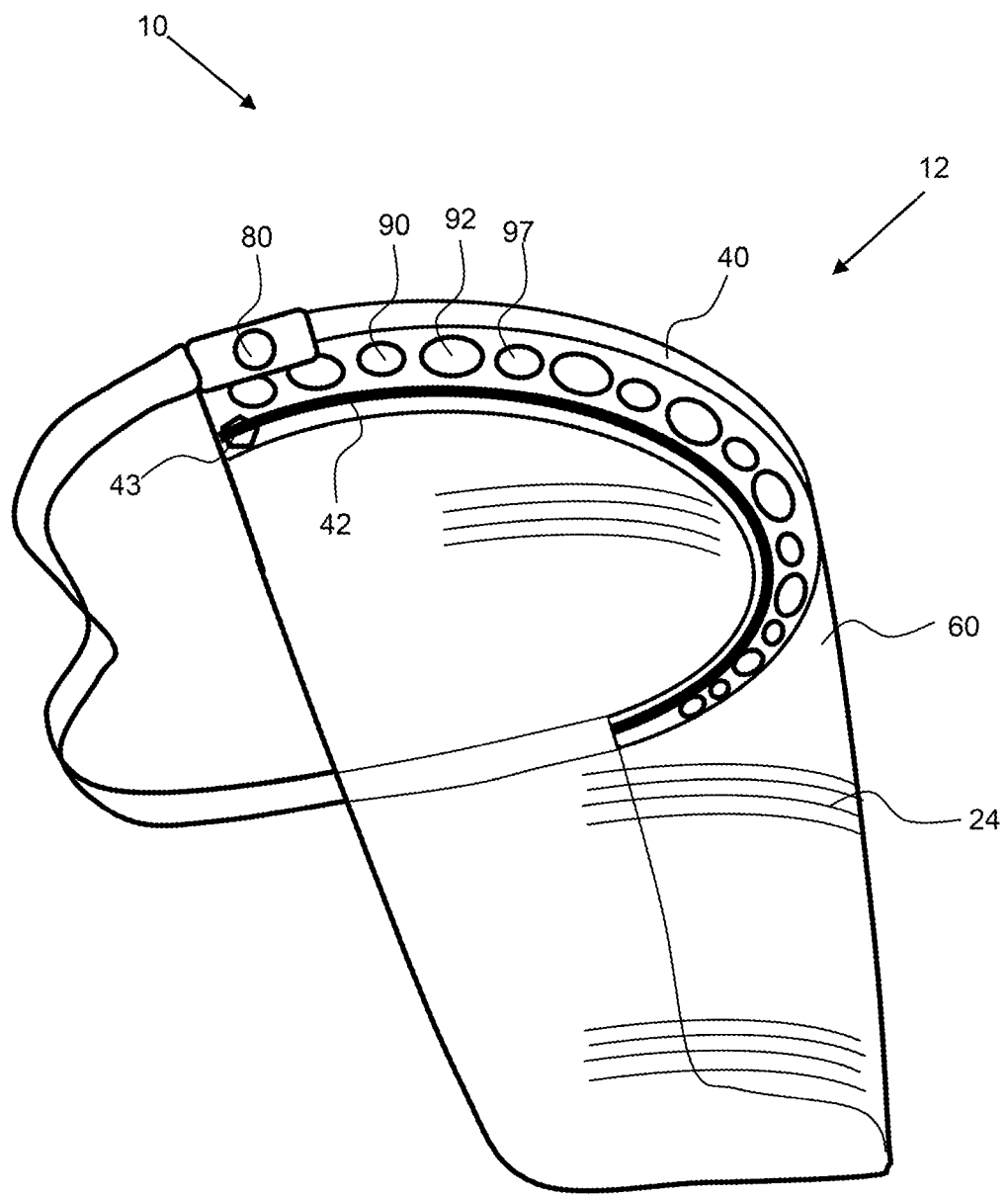
Figure 4:
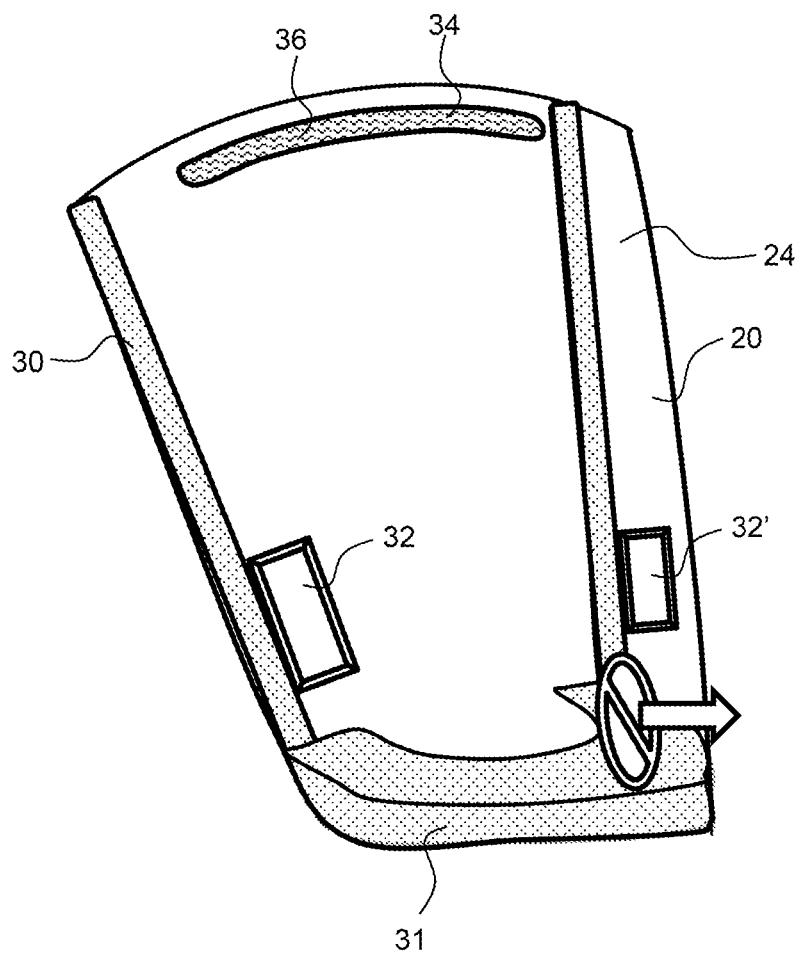
Figure 5:
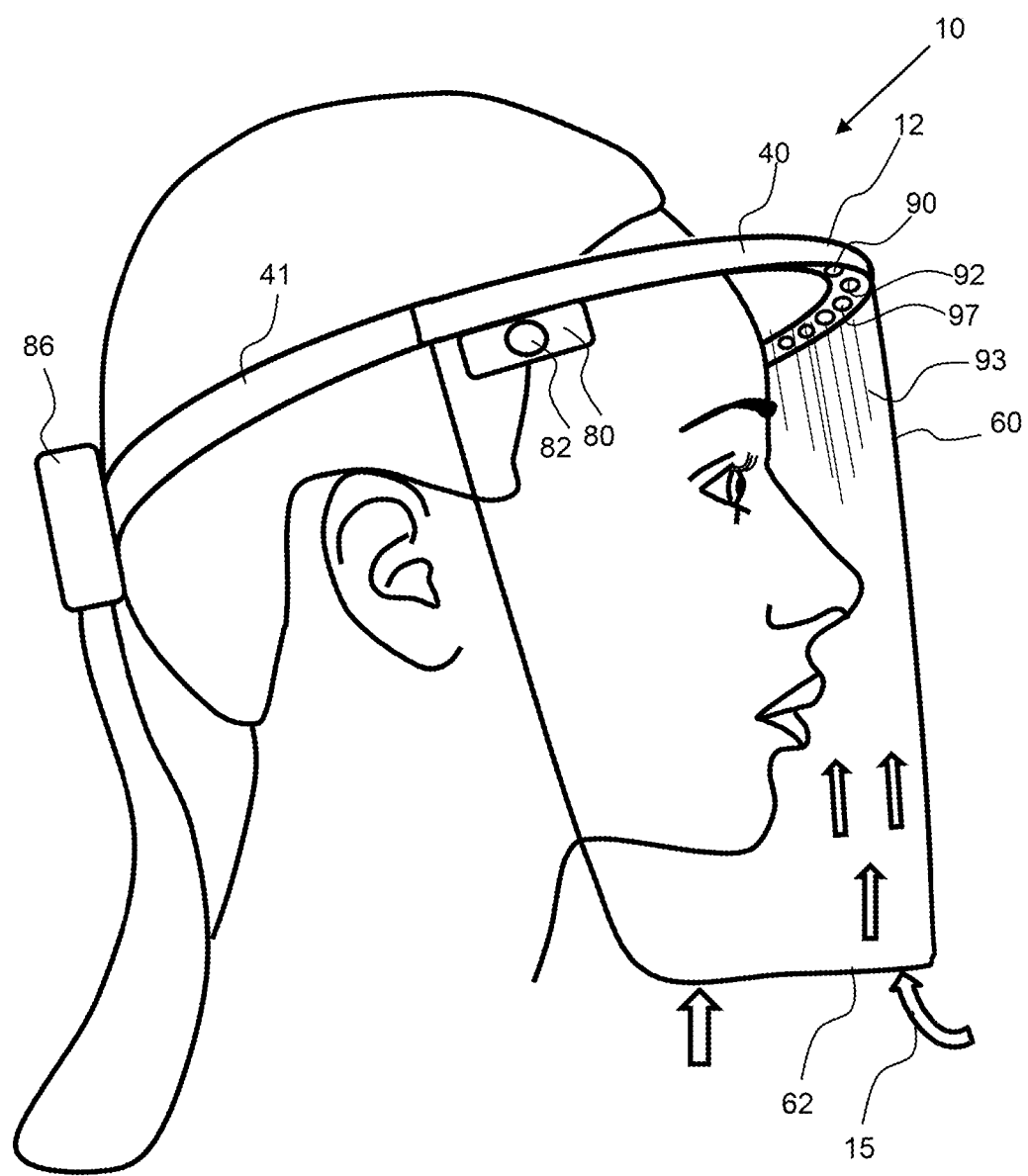
Figure 6:
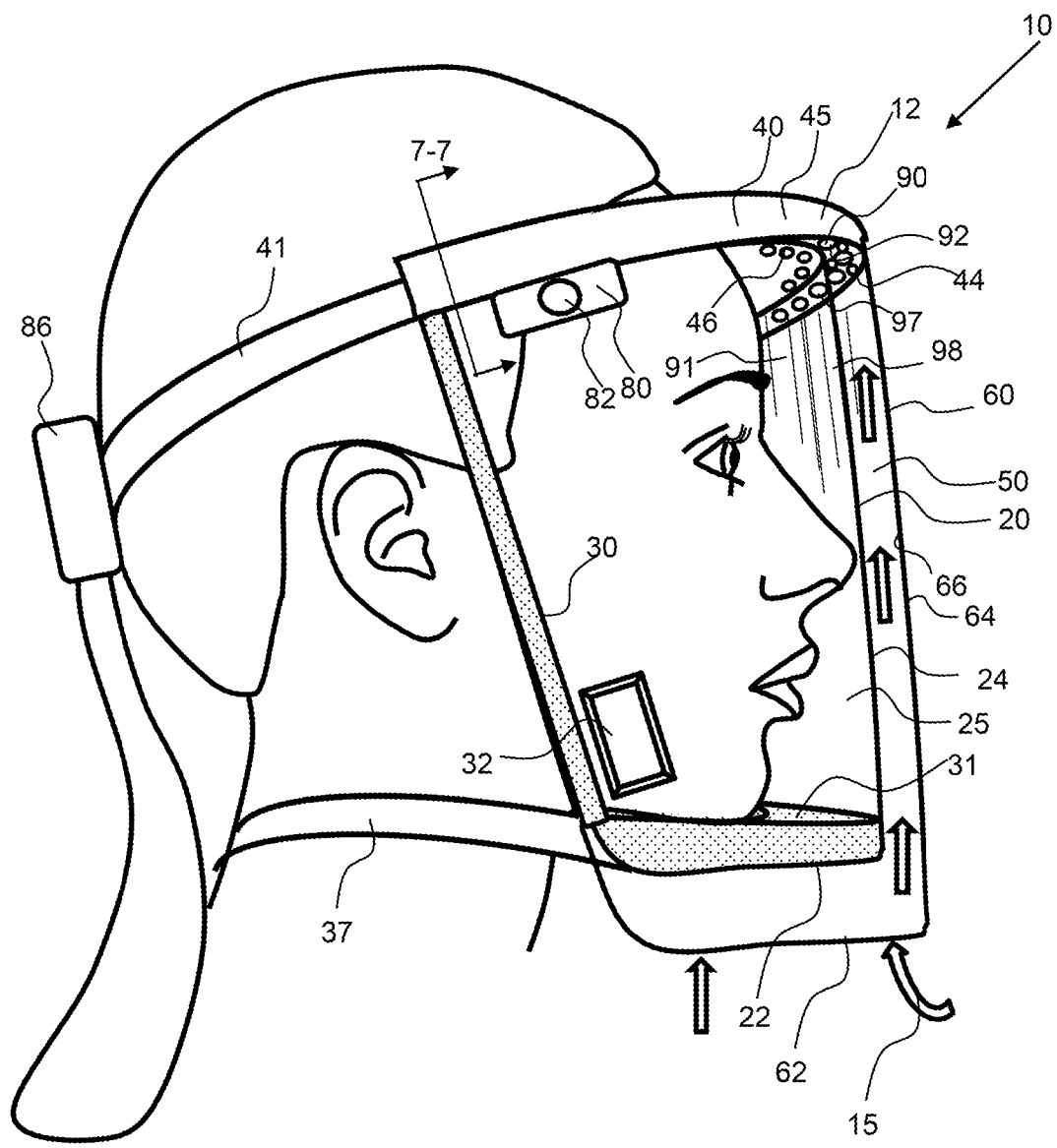

U.S. provisional patent No. 63/026,003, to Fulbrook, shows an exemplary ultraviolet disinfecting cartridge coupled with a face shield in FIGS. 4, 5 and 6 and the components of the exemplary ultraviolet disinfecting cartridge is shown in FIG. 3 and described in the specification, which is incorporated herein by reference. Any of the exemplary ultraviolet disinfecting cartridges may be incorporated into the face shield as described herein. In addition, any of the components shown and described in FIG. 3 for the exemplary ultraviolet disinfecting cartridge are incorporated by reference herein and may be configured in the exemplary ultraviolet disinfecting cartridge or headgear plenum as described herein.

A first embodiment of the present invention has a more open plenum design with an outer shield and a partial inner shield configured inside of the outer shield and proximal to the wearer's face, to create a plenum where the airflow and UV exposure takes place between the shields. The inner shield is detachably attachable and extends down to near the wearer's eyebrow level where the shield barrier deflects any UV away from the wearer's face to avoid eye and skin exposure. This design uses a narrow band 222 nm UV light emitter, which has been shown to be eye and skin safe for humans to provide an effective neutralizing effect on pathogens such that the bonds and atomic structure in the virus conformationally change with UV absorption to render it harmless.

A second embodiment of the present invention has a closed cartridge design that has a channel for disinfecting incoming air and generally extends across the forehead at the top of the shield. In this embodiment, UV light emission may be totally contained within the cartridge and two narrow band LED UV emitters may be used: a UV neutralizing light emitter producing a UV light with a wavelength of substantially 222 nm, and a pathogen destroying UV emitter producing a UV light with a wavelength of substantially 250-280 nm UVC range, which is known to break the structural bonds in a pathogen to destroy it. A coating of Titanium Dioxide may be configured within the cartridge where the UV lights are located and may act as an effective catalyst that facilitates UV absorption by pathogens.

Both of these embodiments have inlets for receiving inlet breathing air that is then disinfected by UV light before being channeled into the face shield for breathing. Both embodiments may have fans to control airflow and HEPA filters proximal to the inlets for the breathing air and optionally at the outlets. Both embodiments may also have an ionizer system that has been shown to be an effective disinfectant and air purifier. The ionizer system is composed of an ionizer emitter near the intake port and a collector bar for binding ionized particles near the outlet port. The ionizing and UV emission methods both produce a small amount of ozone as a by-product. Ozone is also an effective disinfectant. Since ozone can have negative effects on some users, an ozone catalyst such as Manganese Oxide (transition metal oxides) is used along the surface of the channel near the outlet port to capture and convert ozone to ensure the ozone level of breathing air is safe and below FDA standards. Once the airflow passes through the UV LED "kill zones" between the baffles in the channel, stray UV light may be captured by a catalytic coating such as Zinc Oxide or flat black paint that will prevent it from escaping through the outlet port.

The cartridge may have an arrangement of baffles that produces a serpentine airflow channel that increase the resonance time of the breathing air within the breathing air disinfecting cartridge. The walls of the cartridge and/or the baffles may be polished and have dimples as irregular surfaces, as it has been shown that a more random scatter of UV photons increases the probability of capture by a pathogen molecule. The use of two UVC/UVGI wavelengths, an ionizer, and a small amount of ozone multiply the disinfection effect, as each targets different areas of the molecular structure, especially the RNA or DNA of the pathogen. When the airflow rate exposes pathogens for at least 100 milli-seconds or more in the serpentine channels, research has shown that the 99.9% disinfection rate will be achieved, especially when the UV LED emitters are proximal to the pathogens within the airflow channel. In effect, both embodiments actively and effectively neutralize pathogens (viruses, bacteria, and fungi).

To summarize the cartridge embodiment components according to airflow through the cartridge: inlet port consisting of louvers, a filter, a fan, an ionizer emitter, a tube with baffles (polished and dimpled surfaces) that disrupt airflow and increase dwell time within "kill zones" where alternating UV LEDs are present with a Titanium Oxide coating, a UV absorbing surface such as a coating of Zinc Oxide, a coated flat black painted surface that also absorbs stray UV photons, a coated surface of an ozone catalyst (e.g., Manganese Oxide) to convert $O_3$ to $O_2$, a plate for collecting ionized particles, an optional filter, and the output port where disinfected, purified breathing air is released within the face shield. The method of use may be controlled by a switch and indicators that will allow the user to select disinfection means and the system may be powered by a remote battery pack. In summary, the principle of redundancy where two UVC/UVGI dominant wavelength sources, an ionizer with a collector plate, and a small amount of ozone by-product greatly enhance the rate constant of pathogen neutralization to where the industry statistical standard of 99.9% disinfection will be readily achieved within the plenum channel or cartridge embodiments as the breathing air passes through the airflow channels.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

FIG. 1 shows a side view of a person wearing an exemplary ultraviolet light disinfecting face shield having an air plenum configured between an outer shield and an inner shield and a plurality of ultraviolet lights configured to emit light into this plenum and disinfect incoming air before the person inhales the air in.

FIG. 2 shows a bottom view of an exemplary ultraviolet light disinfecting face shield having an air plenum configured between an outer shield and an inner shield and a plurality of ultraviolet lights configured to emit light into this plenum and disinfect incoming air.

FIG. 3 show a perspective view of an exemplary inner shield of the ultraviolet light disinfecting face shield.

FIG. 4 shows a perspective view of an exemplary inner shield having an inlet with an inlet filter configured thereover and one-way exhaust valves.

FIG. 5 shows a side view of a person wearing an exemplary ultraviolet light disinfecting face shield with the inner shield removed and a neutralizing UV light emitting down from a neutralizing UV light emitter.

FIG. 6 shows a side view of a person wearing an exemplary ultraviolet light disinfecting face shield having an air plenum configured between an outer shield and an inner shield and a plurality of ultraviolet lights configured to emit light into this plenum and disinfect incoming air before the person inhales the air.

FIG. 7 shows a cross sectional view of the headgear and headgear plenum taken along line 7-7 in FIG. 6.

FIG. 8 shows a cross sectional view of the headgear and headgear plenum taken along line 8-8 in FIG. 7 and is shown without some of the components for ease of illustrating the airflow channel extending within the headgear plenum.

FIG. 9 shows a cross sectional view of the headgear and headgear plenum taken along line 8-8 in FIG. 7 and shows breathing air disinfecting components within the headgear plenum.

FIG. 10 shows a side view of a person wearing an exemplary ultraviolet light disinfecting face shield having a headgear with an inlet to receive inlet breathing air and a headgear air outlet for delivering disinfected breathing air from the headgear into the interior of the face shield and an exhaust fan and filter for exhausting exhaled air from the face shield.

FIG. 11 shows a perspective view of an exemplary ultraviolet light disinfecting face shield having an outer shield with a front protrusion that extends out from the headgear and has a non-linear profile to provide additional space or breathe distance between the mouth and the interior of the outer shield.

FIG. 12 shows a bottom view of an exemplary ultraviolet light disinfecting face shield having a headgear plenum within the headgear for disinfecting air before it is delivered into the interior of the face shield.

FIG. 13 shows a cross sectional view of the headgear and headgear plenum taken along line 13-13 in FIG. 10.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, an exemplary ultraviolet light disinfecting face shield system 10 comprises an outer shield 60 and an inner shield 20 having a UV light protection barrier 24. The outer shield and an inner shield are coupled with headgear 40 that may have a head gasket 48 to seal the headgear to the person's head, when donned. An air plenum 50 is configured between the outer shield and an inner shield and a plurality of ultraviolet light emitters 90 are configured in the headgear 40 to emit UV light 91 into this plenum to disinfect incoming air before the person inhales the air. The outer shield extends down to an extended end 62 that extends further down that the extended end 22 of the inner shield. A face gasket 30 extends from the inner shield to the person's face and a chin gasket 31 extends from the inner shield around the person's chin or to produce an effective seal between the person's face and the inner shield. A gasket strap 37 may be used to secure the inner face shield and face gasket to the person's face to effectively seal the inner shield to the person's face.

Breathing air 15 enters into the air plenum inlet 26, an opening between the inner shield 20 and outer shield 60, through the air plenum 50 and travels up toward the UV light emitter 90 where viruses are effectively neutralized and/or destroyed by exposure to the UV light. A plurality of UV light emitters may be configured to emit light into the plenum. In an exemplary embodiment, the UV light emitter is a neutralizing UV light emitter 92 producing UV light having a wavelength that is skin-safe, such as about 222 nm, or a destroying UV emitter 97, producing a UV light 91 having a wavelength that destroys viruses, such as about 270 nm+/−10 nm. The disinfected air passes through the air inlet 34 of the inner shield where the person inhales the air. The air inlet may include an inlet filter 36 that may prevent UV light from entering inside area 25 of the inside shield 20 and to filter particles and moisture droplets from entering into the inside surface of the inner shield. When the person exhales, the exhaled air passes through one or more one-way exhaust valves 32 that allow air to exit the inner shield but effectively prevents air from entering the inner shield. A battery 86 may configured to power the UV light emitters and controller of the ultraviolet light disinfecting face shield system 10 and may be configured on the head strap 41 to balance the weight of the ultraviolet light disinfecting face shield 12 with the battery 86. A neck strap 37 may also secure the exemplary ultraviolet light disinfecting face shield around a person's head and secured over their face. The neck strap may pull the chin gasket around a person's chin.

A person may use the user interface 82 of the controller 80 to switch from destroying UV light to neutralizing UV light. An inner shield receiver may be configured to receive the inner shield and an inner shield sensor may detect when the inner shield is attached. The controller may only allow the destroying UV light to be emitted when the inner shield is attached, as it provides a barrier between the destroying UV light and the person's face and eyes.

Figure 2:
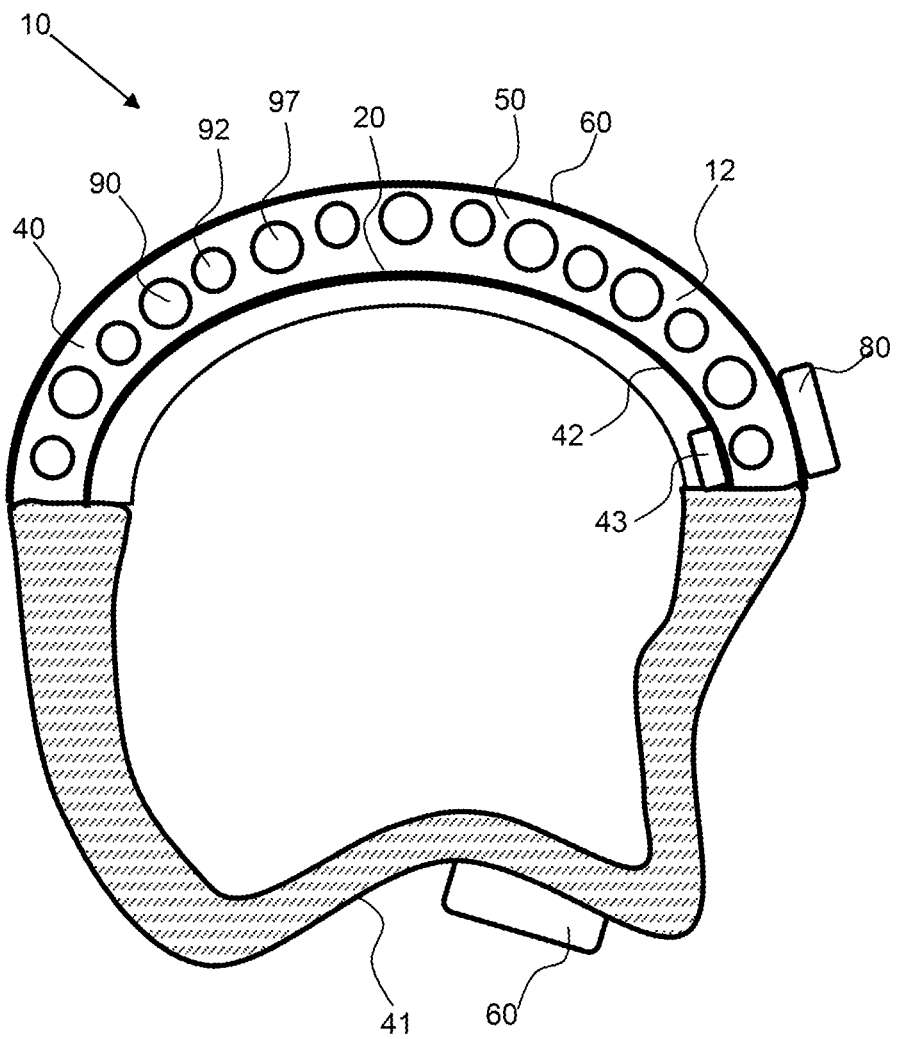

Referring now to FIGS. 2 and 3, the UV light emitters 90 in the headgear include a neutralizing UV light emitter 92 and destroying UV light emitter 97, each emitting a different wavelength of UV light and described herein. The light emitters emit light down along the inside surface of the outer shield, or in the air plenum 50 between the outer shield 60 and inner shield 20. A controller 80 may be used to change the type of UV light that is emitted. An inner shield may protect a person's face from exposure to UV light that may be harmful, such as the destroying UV light. Therefore, the destroying UV light emitters may be deactivated unless the inner shield 20 is inserted into the inner shield receiver 42 of the headgear 40. An inner shield sensor 43 may detect when the inner shield is attached and the controller 80 deactivate the destroying UV light emitters when the inner shield is not attached. A person may use the controller to switch from neutralizing UV light, destruction UV light or a combination of both when the inner shield is attached. As shown in FIG. 3, the inner shield is removed and only the outer shield 60 extends down from the headgear 40. A person may utilize this configuration to provide UV light disinfection over their face and breathing air.

As shown in FIG. 4, an exemplary inner face shield 20 is configured with a pair of one-way exhaust valves 32, 32' and an air inlet 34 for receiving neutralized air therethrough. The inner shield has a face gasket 30 comprising a chin gasket 31 to produce an effective air seal around a person's face. A gasket may also be configured around the headgear to produce a seal along the person's head, such as along at least the forward part of the headgear.

As shown in FIG. 5, a person is wearing an exemplary ultraviolet light disinfecting face shield 12 with the inner shield 20 removed and a neutralizing UV light 93 emitting down from a neutralizing UV light emitter 92 to treat the breathing air 15 as it enters inside of the outer shield 60.

As shown in FIG. 6, an exemplary ultraviolet light disinfecting face shield system 10 comprises an outer shield 60 and an inner shield 20. An air plenum 50 is configured between the outer shield and an inner shield and a plurality of ultraviolet light emitters 90 are configured in the headgear 20 to emit UV light 91 light into this plenum to disinfect breathing air 15 before the person inhales the breathing air. The outer shield extends down to an extended end 62 that extends further down than the extended end 22 of the inner shield. The outer shield has an outer side 64 and an inner side 66 along the air plenum 50. A face gasket 30 extends from the inner shield to the person's face and a chin gasket 31 extends from the inner shield around the person's chin to produce an effective seal between the person's face and the inner shield. Breathing air 15 enters into the plenum and travels up toward the UV light emitter 90 where viruses are effectively neutralized and/or destroyed by exposure to the UV light. A plurality of UV light emitters may be configured to emit light into the plenum. Note that with the inner shield attached, the destroying UV light emitters 97 may emit a destroying UV light 98. The neutralizing UV light emitters 92 may emit a neutralizing UV light as well, or in combination with the destroying UV light. In an exemplary embodiment the UV light emitted is a neutralizing UV light having a wavelength that is skin-safe, such as about 222 nm, or a UV destroying UV light having a wavelength that destroys viruses, such as about 270 nm+/−10 nm, or a combination of both. The disinfected air passes through the headgear inlet 44 of the headgear and up into a headgear plenum 45 in the headgear before passing through the headgear air outlet 46 and into the inside area 25 of the inner shield 20, where the person inhales the disinfected air.

Figure 7:
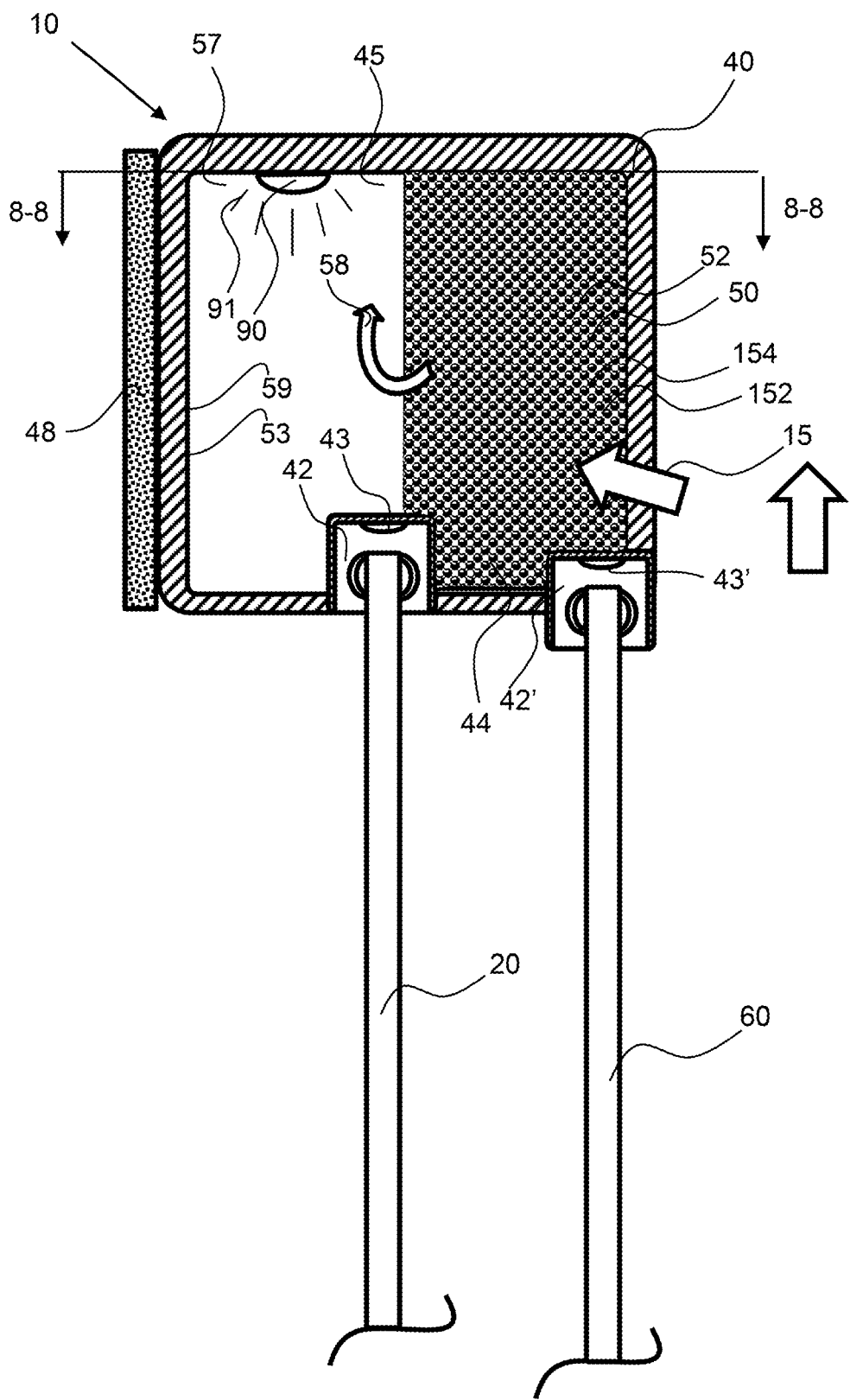

Referring now to FIGS. 7 to 9, an exemplary ultraviolet light disinfecting face shield system 10 may comprise a breathing air disinfecting cartridge 57 that has a headgear air inlet 44 for receiving breathing air from the air plenum 50, serpentine airflow channel 58 formed by an arrangement of headgear plenum baffles 52 and a plurality of UV light emitters to disinfect the breathing air 15 before exiting through the headgear air outlet 46 and into the inside area 25 of the inner shield 20 for breathing. The baffles may have a textured surface, such as a dimpled surface 152 configured to disperse the UV light in a wide range of directions. The baffle surface may be a polished surface 154 having a surface roughness Ra of about 10 µm or less, about 5 µm or less, about 2.5 µm or less, about 1.0 µm or less, about 0.5 µm or less, about 0.2 µm or less, and any range between and including the surface roughness values provided. The headgear plenum may extend along a front of an ultraviolet light disinfecting face shield system 10, or over a person's forehead when donned or may extend around a portion of the person's head. The headgear plenum may extend around the back of a person's head or along the head strap 41 from a first side of the face shield to the opposing second side of the face shield.

As shown in FIG. 7, an inner shield 20 is detachably attachable to the headgear 40 by insertion and removal into the inner shield receiver 42. A ball and detent arrangement may be configured to secure the inner shield 20 to the headgear 40. An inner shield sensor 43 is configured to sense when the inner shield is inserted into the inner shield receiver and is coupled with the controller. As shown in FIG. 7, the headgear plenum 45 has a headgear air inlet 44 for receiving the breathing air 15 from the air plenum 50 configured between the inner shield 20 and outer shield 60. The breathing air 15 is directed by the baffle 52 along the headgear plenum serpentine airflow channel 58. A plurality of UV light emitters may be configured along the headgear plenum serpentine airflow channel 58 to disinfect the breathing air. The UV light emitters may be configured such that no direct UV light is emitted from the UV light emitter out of the headgear plenum. The interior of the headgear plenum 45 may have a UV catalyst 59 producing a UV catalyst absorption surface that is configured to react with UV light to further disinfect pathogens or to absorb the UV light. The inside wall of the headgear plenum may also have a reflector 53 producing reflective surfaces over a portion of the interior. The head gasket 48 is configured to produce an effective seal along a person's head, such as along their forehead.

Figure 10:
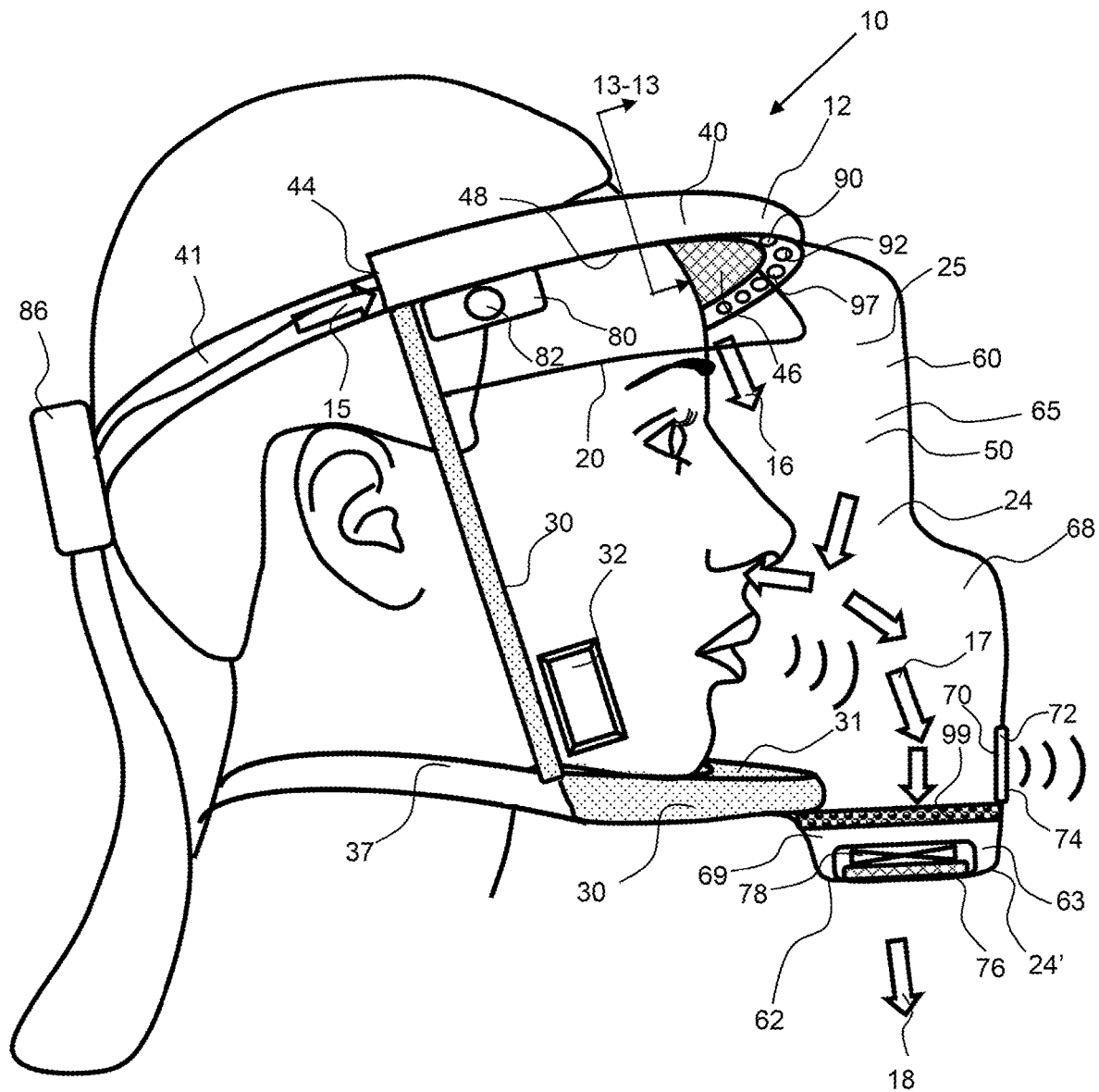

As shown in FIG. 8, the headgear 40 has a headgear plenum 45 for disinfecting the breathing air between and headgear air inlet 44 and headgear air outlet 46. The breathing air flows through the serpentine airflow channel 58 formed by the arrangement of headgear plenum baffles 52, as indicated by the bold curved arrows. The headgear plenum air inlet is, fluidly coupled with or configured to receive breathing air 15. This breathing air may be from the air plenum 50 configured between the outer shield 60 and the inner shield 20, or the breathing air may be from headgear inlet 44 that is in fluid communication with outside air, as shown in FIG. 10. The headgear plenum air outlet 46 is fluidly coupled with the inside area 25 of the inner shield 20, or the inside area 65 of the outer shield 60 when the inner shield is detached, or the area proximal a person's face when donned to deliver disinfected breathing air 16 into the interior of the face shield. The headgear plenum 45 extends from a right end 47 to a left end 49 and has enough length to effectively disinfect the breathing air. As noted, the headgear plenum may extend along the front of a person's face when donned and/or may extend around the back of a person's head or along the head strap. The disinfecting components are not shown in FIG. 8 for ease of illustration of the headgear plenum serpentine airflow channel 58.

As shown in FIG. 9, the headgear plenum 45 comprises a plurality of UV light emitters 90 that emit UV light 91 into the serpentine airflow channel 58. There may be two types of UV light emitters, a neutralizing UV light emitter 92 and a destroying UV light emitter 97, as described herein. The different types of UV light emitters may be configured in an alternating arrangement as the air flows through the headgear plenum. The UV light emitters are preferably destroying UV emitter 97, producing a UV light having a wavelength that destroys viruses, such as about 270 nm+/−10 nm. A portion of the interior of the headgear plenum 45 may be coated with a UV reactant 112, such as titanium dioxide, that aids in disinfecting the breathing air as it flows through the headgear plenum. A UV light absorption material 114, such zinc oxide, or a non-reflective material 116, such as flat black paint, may be configured within the interior of the headgear plenum, such as proximal to the headgear air outlet 16, to absorb the UV light and prevent UV light from exiting the plenum.

An ionizer 56 may be configured proximal to the headgear plenum air inlet 44 to introduce ions into the airflow. An ionizer produces disinfecting ionization of particulate matter and pathogens in the flow channel and may produce a minimal amount of ozone, which is also known to react with organic compounds, such as pathogens to disinfect the breathing air and/or exhalation air. The ions may more effectively aid in disinfecting the air as it flows through the airflow channel. An ionizer plate 51 is configured proximal to the headgear air outlet 46 to react with any ions and to prevent ions from passing through the outlet. Also, an ozone catalyst 118 may be configured in the interior of the headgear plenum, such as proximal the outlet, to react with any ozone to prevent the ozone from passing out of the headgear air outlet 16.

An inlet filter 36 may be configured proximal to the headgear air inlet 44 to filter out particles and moisture from the inlet breathing air 15. An arrangement of baffles 52 produces a serpentine airflow channel 58 that increase the resonance time of the breathing air within the breathing air disinfecting cartridge 57. An outlet filter 54 may be configured within the headgear plenum and may be proximal to the headgear plenum air outlet 46. The outlet filter 54 may be configured to remove particles and aerosol droplet from the breathing airflow before it enters into the inside area 25 for breathing. The ionizer and/or filter may be replaceable from the breathing air disinfecting cartridge 57. The head gasket 48 extends along the inside of the headgear plenum to form a seal along a person's head when donned. As shown in FIG. 9, the inside surface may comprise a reflector 53, 53' that is configured to reflect the UV light. The reflector 53 may be on the wall or a reflector 53' may be on a baffle. The reflectors may be configured away from the headgear plenum inlet 44 and headgear plenum air outlet 46.

As shown in FIG. 10, an exemplary ultraviolet light disinfecting face shield system 10 comprises an outer shield 60 having a UV light protection barrier 24. The outer shield is coupled with headgear 40 that has a head gasket 48 to seal the headgear to the person's head, when donned to produce an inside area 65 within the outer shield. A plurality of ultraviolet light emitters 90 are configured in the headgear 40 to emit UV light into the interior of the face shield to disinfect air before the person inhales the air. The outer shield extends down to an extended end 62. A face gasket 30 extends along the interior of the outer shield to the person's face and a chin gasket 31 extends from the outer shield around the person's chin to produce an effective seal between the person's face and the outer shield. A gasket strap 37 may be used to secure the inner face shield and face gasket to the person's face to effectively seal the inner shield to the person's face.

Breathing air 15 enters into the headgear 40, through the headgear air inlet 44 and travels through the headgear plenum wherein the inlet breathing air is disinfected by UV light emitters 90 that produce UV light 91, within the headgear plenum, as shown in FIG. 9. The inlet breathing air is disinfected within the headgear plenum, where viruses are effectively neutralized and/or destroyed by exposure to the UV light 91. The disinfected breathing air 16 is exhausted out of the headgear air outlet 46 and into the interior of the face shield. A plurality of UV light emitters may be configured to emit light into the face shield as well to further disinfect the breathing air, including any air that may have passed through the gaskets. In an exemplary embodiment, the UV light emitter is a neutralizing UV light emitter 92 producing UV light having a wavelength that is skin-safe, such as about 222 nm, or a destroying UV emitter 97, producing a UV light 91 having a wavelength that destroys viruses, such as about 270 nm+/−10 nm. The disinfected air passes through the headgear air inlet 44 configured along headgear 40. The air inlet may include an inlet filter 36 to filter particles and moisture droplets from entering into the headgear plenum 45, as shown in FIG. 9. A fan or other plenum air moving device 55 may draw inlet breathing air 15 in through the headgear air inlet 44 and force it down into the interior of the face shield, or inside area of the face shield, as disinfected breathing air 16.

As shown in FIG. 10, the disinfected breathing air may be inhaled and the exhaled air 17 will be forced out of the interior of the face shield by an exhaust fan 78. An exhaust filter 76 and exhaust fan 78 may be configured along the bottom of the face shield and may be configured in an exhaust protrusion 69, that extends from the bottom of the face shield. In this way, forced air flows down from the top of the disinfecting face shield system 10 or top of the interior of the face shield to the bottom of the face shield. This downward directional flow may prevent fogging of the mask and may enable easy inhalation as no vacuum is formed within the interior of the face masks. An exhaust UV emitter 99 may be configured to emit UV light on exhaled air 17 in the inside area 25 of the face shield, such as down into the exhaled air 17 as it approaches the exhaust filter 76 and/or exhaust fan 78 or as it exits the exhaust filter and/or exhaust fan. If a person is breathing very hard, the exhaled air may pass through one or more one-way exhaust valves 32 that allow air to exit the inner shield when a threshold pressure is surpassed within the interior of the face shield. The one or more one-way exhaust valves may allow air to vent but effectively prevents air from entering the interior of the face shield. The exhaust UV emitter 99, and/or exhaust filter and/or exhaust fan may be configured proximal to the extended end 62 of the outer face shield, such as in a shield exhaust plenum 63, as shown. The exhaust plenum may have a UV light protection barrier 24' configured to prevent the UV light from the exhaust UV emitter 99 from being emitted outside from the face shield.

A battery 86 may configured to power the UV light emitters, controller, fans, air moving devices and the like of the ultraviolet light disinfecting face shield system 10 and may be configured on the head strap 41 to balance the weight of the ultraviolet light disinfecting face shield 12 with the battery 86. A neck strap 37 may also secure the exemplary ultraviolet light disinfecting face shield around a person's head and secured over their face. The neck strap may pull the chin gasket around a person's chin.

A person may use the user interface 82 of the controller 80 to switch the system on where destroying UV light, neutralizing UV light, and/or the ionizer are on, or where only one of the UV light types is on and the ionizer may be switched off. The user interface may enable the user to turn on the destroying UV light emitters 97 and the neutralizing UV light emitters 92 without the ionizer, or just the destroying UV light emitters 97 or just the neutralizing UV light emitters 92 with or without the ionizer. The user may be able to turn the UV light emitters off along with the ionizer. An inner shield receiver may be configured to receive the inner shield and an inner shield sensor may detect when the inner shield is attached. The controller may only allow the destroying UV light to be emitted when the inner shield is attached, as it provides a barrier between the destroying UV light and the person's face and eyes.

Figure 11:
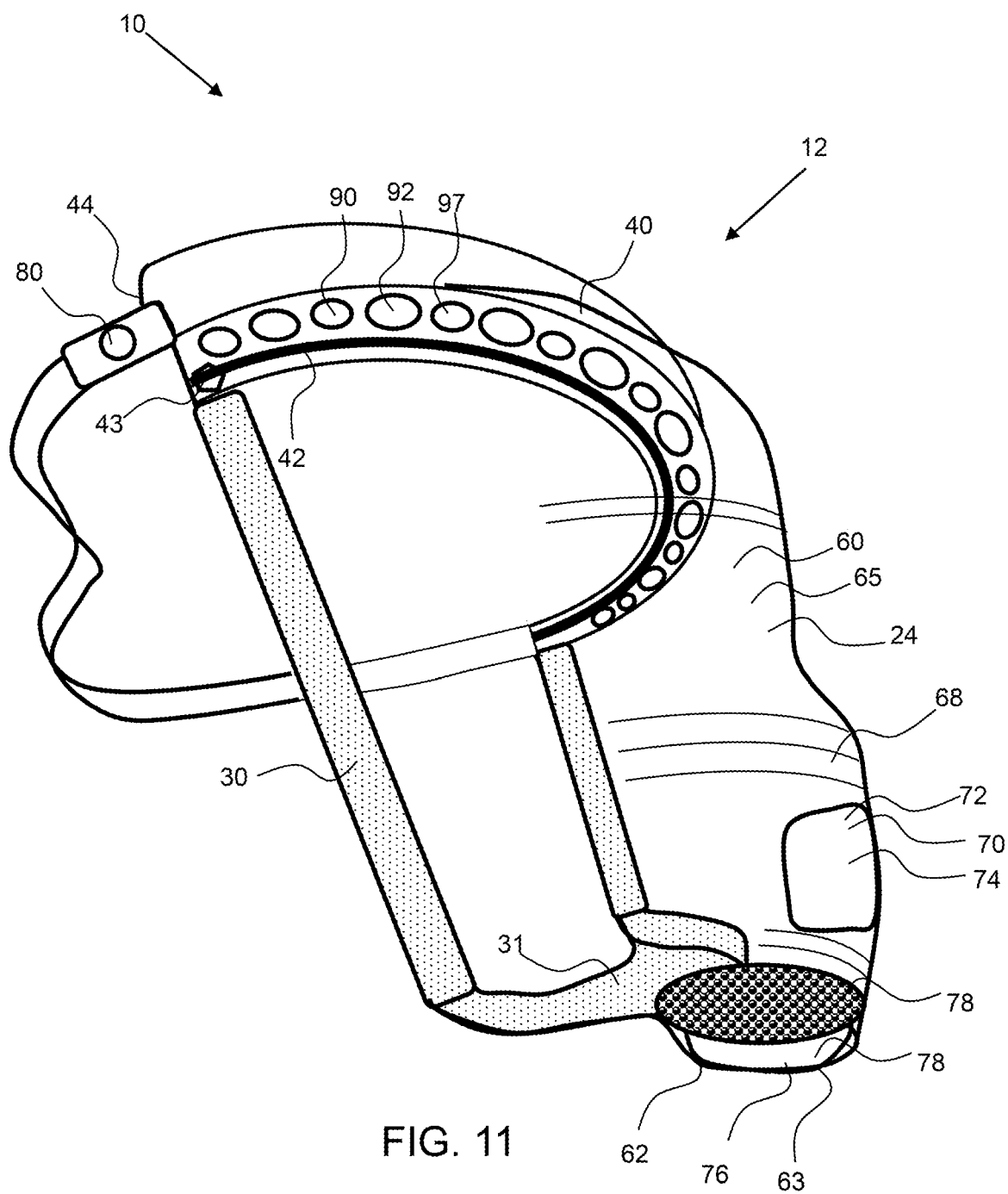
Figure 12:
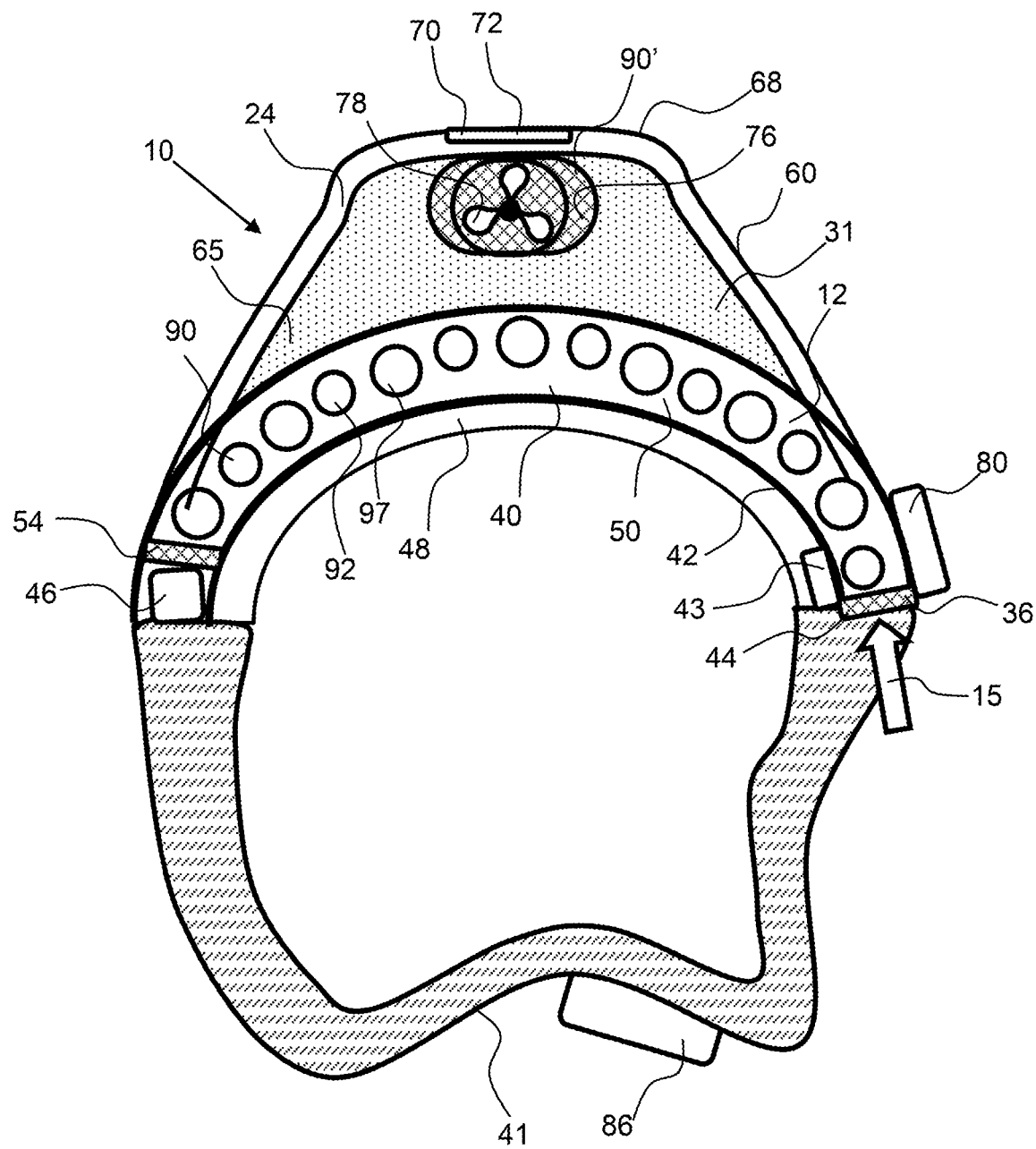

Referring now to FIGS. 11 and 12, the UV light emitters 90 in the headgear include a neutralizing UV light emitter 92 and destroying UV light emitter 97, each emitting a different wavelength of UV light and described herein. The light emitters emit light down along the inside surface of the outer shield, or in the air plenum 50 between the outer shield 60 and inner shield 20. A controller 80 may be used to change the type of UV light that is emitted. An inner shield may protect a person's face from exposure to UV light that may be harmful, such as the destroying UV light. Therefore, the destroying UV light emitters may be deactivated unless the inner shield 20 is inserted into the inner shield receiver 42 of the headgear 40. An inner shield sensor 43 may detect when the inner shield is attached and the controller 80 deactivates the destroying UV light emitters when the inner shield is not attached. A person may use the controller to switch from neutralizing UV light, destruction UV light or a combination of both when the inner shield is attached. As shown in FIG. 3, the inner shield is removed and only the outer shield 60 extends down from the headgear 40. A person may utilize this configuration to provide UV light disinfection over their face and breathing air. The ultraviolet disinfecting face shield further comprises an audio enhancement device 70 configured in the outer shield and configured to enhance speech emitted by said person when the ultraviolet disinfecting face shield is donned; wherein the audio enhancement device is a speaker 72.

Figure 13:
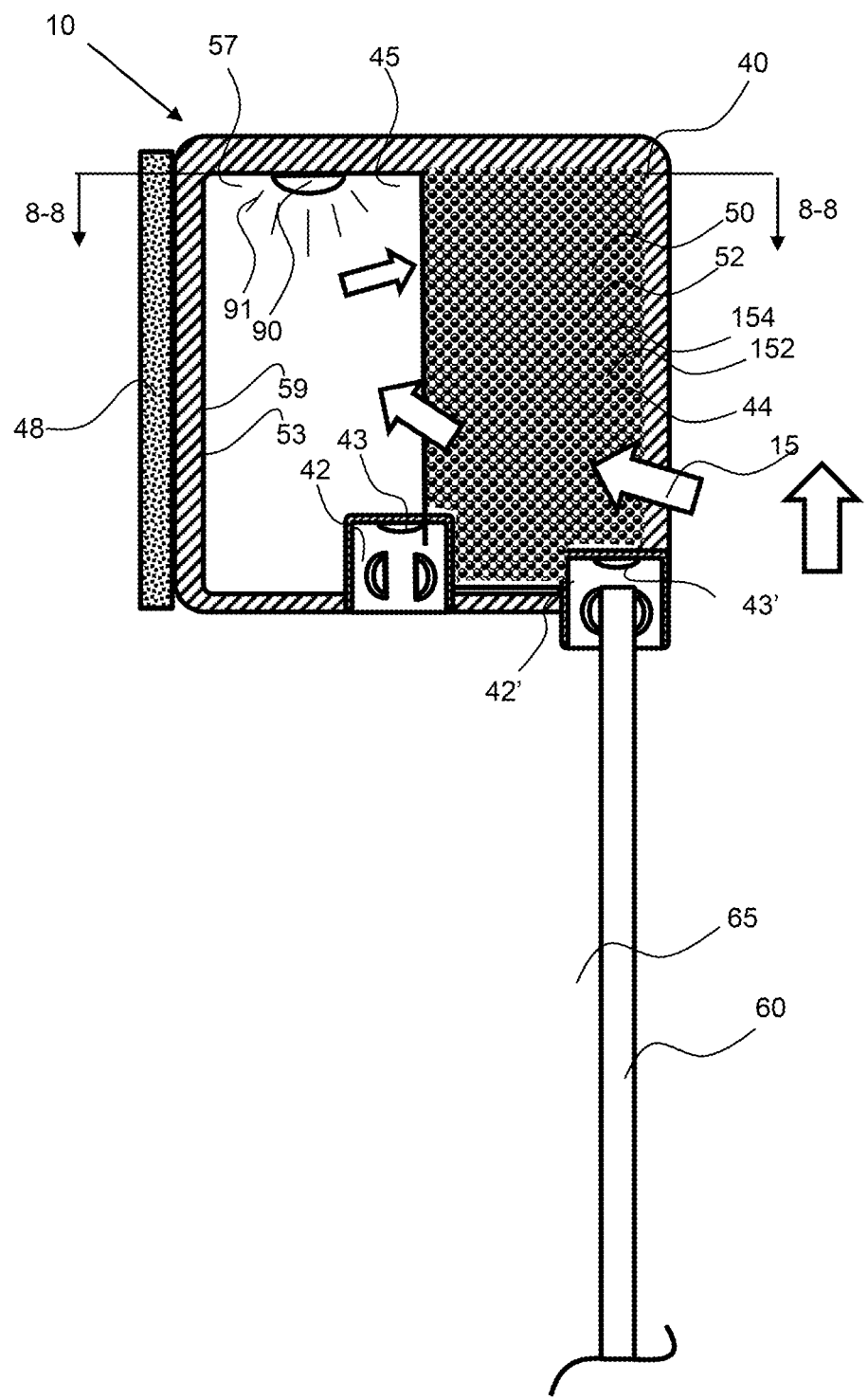

As shown in FIG. 13, the inner shield (not shown) has been detachably attachable to the headgear 40 by removal from the shield receiver 42. A ball and detent arrangement may be configured to secure the outer shield 60 to the headgear 40. An outer shield sensor 43' is configured to sense when the outer shield is inserted into the outer shield receiver 42' and is coupled with the controller. As shown in FIG. 7 and FIG. 13, the headgear plenum 45 has a headgear air inlet 44 for receiving the breathing air 15. The breathing air 15 is directed by the baffle 52 along the serpentine headgear plenum serpentine airflow channel 58. Again, the baffles may have a textured surface, such as a dimpled surface 152 configured to disperse the UV light in a wide range of directions. The baffle surface may be a polished surface 154 having a surface roughness Ra of about 10 μm or less, about 5 μm or less, about 2.5 μm or less, about 1.0 μm or less, about 0.5 μm or less, about 0.2 μm or less, and any range between and including the surface roughness values provided. A plurality of UV light emitters may be configured along the headgear plenum serpentine airflow channel 58 to disinfect the breathing air, as shown in FIG. 9. The UV light emitters may be configured such that no direct UV light is emitted from the UV light emitter out of the headgear plenum. The interior of the headgear plenum 45 may have a UV catalyst 59 producing a UV catalyst absorption surface that is configured to react with UV light to further disinfect pathogens or to absorb the UV light. The inside wall of the headgear plenum may also have a reflector 53 producing reflective surfaces over a portion of the interior.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. An ultraviolet disinfecting face shield system comprising:
   a) an outer shield coupled to a headgear and extending down from the headgear and comprising:
      i) an outer side; and
      ii) an inner side;
   wherein an inside area is formed between the inner side of the outer shield and a person's face when the ultraviolet disinfecting face shield is donned;
   b) the headgear comprising:
      i) a headgear plenum having an inlet for receiving inlet breathing air, said headgear plenum further comprising:
         plenum ultraviolet light emitters configured to emit plenum ultraviolet light into the headgear plenum;
         a plurality of headgear plenum baffles configured to create a serpentine airflow channel for the breathing air flowing therethrough, wherein the breathing air flows around the plurality of baffles while being exposed to the plenum ultraviolet light emitted from the plenum ultraviolet light emitters to produce disinfected breathing air; and
         a plenum air moving device configured to draw said breathing air into the headgear plenum and force said disinfected breathing air into the inside area;
      wherein breathing air is configured to enter the inner side of the outer shield, and
      wherein the plenum ultraviolet light emitters are configured to emit the plenum ultraviolet light onto the disinfected breathing air when donned; and
      ii) a strap coupled to the headgear plenum and configured to extend around a back of a person's head when the ultraviolet disinfecting face shield system is donned on said person's head, and wherein the headgear plenum is configured over the outer shield; and
      iii) a battery that provides power to the plenum ultraviolet light emitters and plenum air moving device;
   an ultraviolet light emitter configured to emit ultraviolet light into the inside area,
   an inner shield and an air plenum configured between the outer shield and the inner shield, wherein the ultraviolet light emitter emits the ultraviolet light into the air plenum.

2. The ultraviolet disinfecting face shield of claim 1, wherein the ultraviolet light has a wavelength of substantially 222 nm.

3. The ultraviolet disinfecting face shield of claim 1, wherein the inner shield has an ultraviolet light protection barrier that filters out ultraviolet light.

4. The ultraviolet disinfecting face shield of claim 3, further comprising a face gasket comprising a chin gasket that is configured to effectively seals the inner shield to a person's face and chin.

5. The ultraviolet disinfecting face shield of claim 1, wherein the plenum ultraviolet light emitters emit ultraviolet light with a wavelength of substantially 270 nm+/−10 nm.

6. The ultraviolet disinfecting face shield of claim 1, wherein the plenum ultraviolet light emitters emit ultraviolet light with a wavelength of substantially 222 nm+/−10 nm.

7. The ultraviolet disinfecting face shield of claim 1, wherein the headgear comprises an inner shield receiver and wherein the inner shield is detachably attachable to the headgear.

8. The ultraviolet disinfecting face shield of claim 7, further comprising an inner shield sensor that detects when the inner shield is attached to the inner shield receiver.

9. The ultraviolet disinfecting face shield of claim 8, further comprising a controller and wherein the controller only enables a neutralizing ultraviolet light emitter to function when the inner shield sensor detects that the inner shield is attached to the inner shield receiver.

10. The ultraviolet disinfecting face shield of claim 9, further comprising a user interface that allows the person to switch from a destroying ultraviolet light emitter that emits ultraviolet light with a wavelength of substantially 270 nm to the neutralizing ultraviolet light emitter that emits ultraviolet light with a wavelength of 222 nm.

11. The ultraviolet disinfecting face shield of claim 1, wherein the headgear plenum is configured as a breathing air disinfecting cartridge that is detachably attachable to the headgear.

12. The ultraviolet disinfecting face shield of claim 11, wherein the headgear plenum comprises an ultraviolet catalyst configured within the airflow channel and configured to receive the ultraviolet light.

13. The ultraviolet disinfecting face shield of claim 12, wherein the ultraviolet catalyst is titanium dioxide.

14. The ultraviolet disinfecting face shield of claim 1, wherein the headgear plenum comprises a filter configured to filter particles out of the breathing air.

15. The ultraviolet disinfecting face shield of claim 1, wherein the headgear plenum comprises an ionizer to produce ions that flow through the serpentine airflow channel.

16. The ultraviolet disinfecting face shield of claim 15, wherein the headgear plenum comprises an ionizer collector plate to react with ions to prevent ions from exiting the headgear plenum.

17. The ultraviolet disinfecting face shield of claim 1, wherein the headgear plenum comprises an ozone catalyst to react with ozone and prevent said ozone from exiting the headgear plenum.

18. The ultraviolet disinfecting face shield of claim 1, further comprising a one-way exhaust valve configured in the outer shield to allow air to exit from the inside area.

19. The ultraviolet disinfecting face shield of claim 1, further comprising an audio enhancement device configured in the outer shield and configured to enhance speech emitted by said person when the ultraviolet disinfecting face shield is donned.

20. The ultraviolet disinfecting face shield of claim 19, wherein the audio enhancement device is a speaker.

21. The ultraviolet disinfecting face shield of claim 1, further comprising an exhaust fan coupled with the outer shield and configured to exhaust exhaled air from the inside area.

22. The ultraviolet disinfecting face shield of claim 21, further comprising an exhaust ultraviolet light emitter, configured to emit ultraviolet light on exhaled air in the inside area.

23. The ultraviolet disinfecting face shield of claim 21, wherein the battery is coupled to the strap of the headgear.

24. The ultraviolet disinfecting face shield of claim 1, wherein the plurality of headgear plenum baffles comprise a textured surface that randomly reflects the plenum ultraviolet light.

25. The ultraviolet disinfecting face shield of claim 24, wherein the plurality of headgear plenum baffles comprise a polished surface having surface roughness, Ra value of less than 0.1 mm.

\* \* \* \* \*